(12) United States Patent
Shan

(10) Patent No.: US 8,733,495 B2
(45) Date of Patent: May 27, 2014

(54) STETHOSCOPE EARPLUG SEAT AND FITTED CONFIGURATION WITH EARPLUG HEAD THEREOF

(76) Inventor: Xijie Shan, Wuxi (CN)

( * ) Notice: Subject to any disclaimer, the term of this patent is extended or adjusted under 35 U.S.C. 154(b) by 358 days.

(21) Appl. No.: 13/126,356

(22) PCT Filed: Jul. 2, 2009

(86) PCT No.: PCT/CN2009/000746
§ 371 (c)(1),
(2), (4) Date: Apr. 27, 2011

(87) PCT Pub. No.: WO2010/124427
PCT Pub. Date: Nov. 4, 2010

(65) Prior Publication Data
US 2012/0053487 A1  Mar. 1, 2012

(30) Foreign Application Priority Data

Apr. 27, 2009  (CN) .......................... 2009 2 0040510

(51) Int. Cl.
*A61B 7/02* (2006.01)
*A61B 7/04* (2006.01)

(52) U.S. Cl.
USPC .............. 181/131; 181/135; 381/67; 600/586

(58) Field of Classification Search
CPC ............ A61B 7/02; A61B 11/08; A61B 7/00; A61F 11/10; A61F 11/12
USPC .................. 600/586; 181/131, 129, 130, 135; 381/67
See application file for complete search history.

(56) References Cited

U.S. PATENT DOCUMENTS

| | | | |
|---|---|---|---|
| 3,882,848 A * | 5/1975 | Klar et al. ..................... | 600/559 |
| 4,852,684 A | 8/1989 | Packard | |
| 5,002,151 A * | 3/1991 | Oliveira et al. ............... | 181/130 |
| 2003/0051939 A1 | 3/2003 | Werblud | |

FOREIGN PATENT DOCUMENTS

| | | |
|---|---|---|
| CN | 2574605 Y | 9/2003 |
| CN | 101172041 A | 5/2008 |
| CN | 101204331 A | 6/2008 |
| CN | 201127108 Y | 10/2008 |

* cited by examiner

*Primary Examiner* — Max Hindenburg
*Assistant Examiner* — Jonathan M Foreman
(74) *Attorney, Agent, or Firm* — Morris, Manning & Martin, LLP; Tim Tingkang Xia, Esq.

(57) ABSTRACT

A stethoscope earplug seat and the fitting a fitted configuration with an earplug head thereof. The stethoscope earplug seat includes a large tubular body (6) and a small tubular body (5). The large tubular body (6) sheaths the outside of the small tubular body (5), and one side of the tube mouth of the large tubular body (6) is level with one side of the tube mouth of the small tubular body (5). The inside radius of the large tubular body (6) is equal to the outside radius of the small tubular body (5), the length of the large tubular body (6) is smaller than the length of the small tubular body (5), and the out-edge part of one side of the small tubular body (5) which is away from the large tubular body (6) is provided with an annular slot (7).

5 Claims, 1 Drawing Sheet

STETHOSCOPE EARPLUG SEAT AND FITTED CONFIGURATION WITH EARPLUG HEAD THEREOF

BACKGROUND OF THE INVENTION

1. Field of Invention

The present invention relates to a medical apparatus part, and more particularly to a stethoscope, and a fitted configuration of an earplug seat and an earplug.

2. Related Art

A stethoscope is an important tool for medical workers to perform medical work. With a sound amplification feature of the stethoscope, a user can know a situation of internal organs of a patient. The stethoscope collects and amplifies a working sound of internal organs of the patient with a head, and then transmits the sound to ears of the user through tubing and earplugs.

Currently, a connection manner of an earplug head and an earplug seat is that the earplug head sheaths the outside of the earplug seat, and is fixed on the earplug seat through an elastic force of the elastic materials of the earplug head. In long-term use, the earplug head falls off easily. Furthermore, the earplug seat has to be replaced at the same time when the earplug head is being replaced, so the resources are wasted.

SUMMARY OF THE INVENTION

Accordingly, the present invention is directed to an earplug seat, so as to facilitate fixation of an earplug head, so the earplug head does not fall off easily, the earplug seat may be reusable, and the resources are saved.

Furthermore, the present invention is directed to a fitted configuration of an earplug seat and an earplug head. The fitted configuration of an earplug seat and an earplug head can be easily installed, so as to facilitate fixation and replacement of the earplug head, and the earplug head does not fall off easily, and the earplug seat and the earplug head may have a match of two colors.

The purpose of the present invention is implemented as follows. One solution of the present invention is as follows.

A stethoscope earplug seat includes a large tubular body and a small tubular body. The large tubular body sheaths the outside of the small tubular body, and one side of the tube mouth of the large tubular body is level with one side of the tube mouth of the small tubular body. The inside radius of the large tubular body is equal to the outside radius of the small tubular body, and the length of the large tubular body is smaller than the length of the small tubular body. The out-edge part of one side of the small tubular body which is away from the large tubular body is provided with a second annular slot.

Furthermore, one side of the large tubular body near the second annular slot is provided with a first annular slot. The inside radius of the first annular slot is equal to the inside radius of the large tubular body, and the outside radius of the first annular slot is smaller than the outside radius of the large tubular body.

Furthermore, an inner wall of the small tubular body is provided with a screw thread.

The other solution of the present invention is as follows.

A fitted configuration of an earplug seat and an earplug head includes an earplug head and an earplug seat. The earplug head is integrally formed by connecting a spherical body and an end of a tubular body of the earplug head, and a through hole is formed. The earplug seat includes a large tubular body and a small tubular body, in which the large tubular body sheaths the outside of the small tubular body, and one side of the tube mouth of the large tubular body is level with one side of the tube mouth of the small tubular body; the inside radius of the large tubular body is equal to the outside radius of the small tubular body, and the length of the large tubular body is smaller than the length of the small tubular body. The inside radius of the tubular body of the earplug head is slightly smaller than or equal to the outside radius of the small tubular body. An inner wall of the through hole is provided with an annular convex shoulder, and the out-edge part at the other end of the tubular body of the earplug head is provided with a third annular slot. The out-edge part of one side of the small tubular body is provided with an annular socket a second annular slot, and one side of the large tubular body near the second annular slot is provided with a first annular slot. A part of the small tubular body is placed inside the through hole, and the annular socket second annular slot fits the annular convex shoulder; and a protrusion inside the third annular slot fits and is connected to the first annular slot.

Furthermore, at a side near the second annular slot, a right angle formed between an opening surface of the large tubular body and a surface of the first annular slot parallel to an axis of the large tubular body fits a right angle formed between an outer surface and a side surface of the third annular slot perpendicular to each other.

Furthermore, the outside radius of the large tubular body is equal to the outside radius of the tubular body of the earplug head.

According to the present invention, the earplug head is simply fixed and does not fall off easily, and during replacement of the earplug only the earplug head needs to be replaced without replacing the earplug seat, so as to effectively save the resources; furthermore, the earplug seat and the earplug head may have a match of two colors, so the appearance may be more beautiful.

DETAILED DESCRIPTION OF THE INVENTION

Embodiment 1

Figure 1:
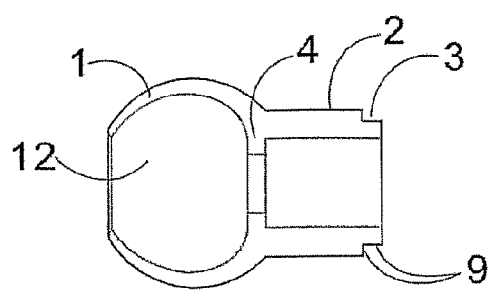
FIG. 1 is a schematic view of an earplug head according to the present invention.
Figure 2:
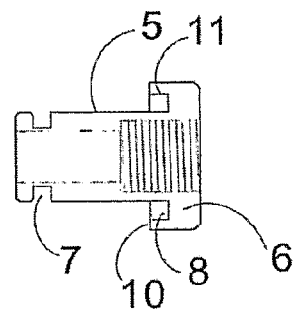
FIG. 2 is a schematic sectional view of an earplug seat according to the present invention.
Figure 3:
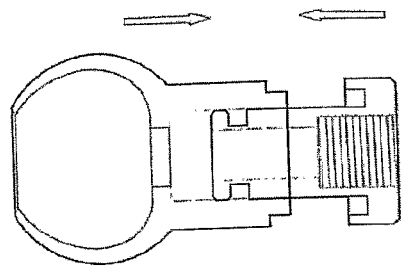
FIG. 3 is a schematic view of an installation process according to the present invention.
Figure 4:
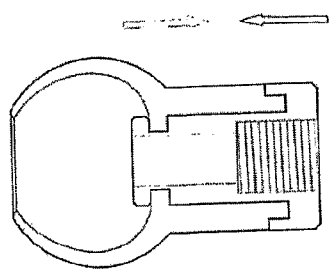
FIG. 4 is a schematic structural view of the present invention.
Figure 5:
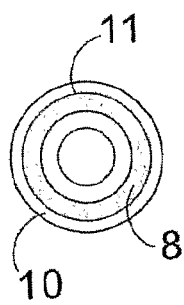
FIG. 5 is a schematic view of an earplug seat according to the present invention.

The present invention is further described with reference to FIG. 2.

A stethoscope earplug seat includes a large tubular body 6 and a small tubular body 5; the large tubular body 6 sheaths the outside of the small tubular body 5, and one side of the tube mouth of the large tubular body 6 is level with one side of the tube mouth of the small tubular body 5. The inside radius of the large tubular body 6 is equal to the outside radius of the small tubular body 5, and the length of the large tubular body 6 is smaller than the length of the small tubular body 5. The out-edge part of one side of the small tubular body 5 which is away from the large tubular body 6 is provided with a second annular slot 7.

Furthermore, one side of the large tubular body 6 near the second annular slot 7 is provided with a first annular slot 8. The inside radius of the first annular slot 8 is equal to the inside radius of the large tubular body 6, and the outside radius of the first annular slot 8 is smaller than the outside radius of the large tubular body 6.

Furthermore, an inner wall of the small tubular body 5 is provided with a screw thread.

Embodiment 2

The present invention is further described below with reference to FIGS. 1, 2, 3, 4, and 5.

A fitted configuration of an earplug seat and an earplug head includes an earplug head and an earplug seat. The earplug head is integrally formed by connecting a spherical body 1 and an end of a tubular body of the earplug head 2, and is formed with a through hole 12. The earplug seat includes a large tubular body 6 and a small tubular body 5, in which the large tubular body 6 sheaths the outside of the small tubular body 5, and one side of the tube mouth of the large tubular body 6 is level with one side of the tube mouth of the small tubular body 5. The inside radius of the large tubular body 6 is equal to the outside radius of the small tubular body 5, and the length of the large tubular body 6 is smaller than the length of the small tubular body 5. The inside radius of the tubular body of the earplug head 2 is slightly smaller than or equal to the outside radius of the small tubular body 5. An inner wall of the through hole 12 is provided with an annular convex shoulder 4, and the out-edge part at the other end of the tubular body of the earplug head 2 is provided with a third annular slot 3. The out-edge part of one side of the small tubular body 5 is provided with a second annular slot 7, and one side of the large tubular body 6 near the second annular slot 7 is provided with a first annular slot 8. A part of the small tubular body 5 is placed inside the through hole 12, and the second annular slot 7 fits and is firmly fastened to the annular convex shoulder 4; and a protrusion inside the third annular slot 3 fits the first annular slot 8.

Furthermore, at a side near the second annular slot 7, a right angle formed between an opening surface 10 of the large tubular body 6 and an outer surface 11 of the first annular slot 8 parallel to an axis of the large tubular body 6 fits a right angle formed between two slot surfaces perpendicular to each other 9 of the third annular slot 3.

An outside radius of the large tubular body 6 is equal to the outside radius of the tubular body of the earplug head 2.

INDUSTRIAL APPLICABILITY

The advantages of the present invention are as follows.

1. As the first annular slot 8 fitted with the third annular slot 3 is configured on the large tubular body 6, a friction coefficient between the earplug head and the earplug seat is effectively increased, so as to make the fitting between the earplug head and the earplug seat firmer.

2. In the fitting between the earplug head and the earplug seat, the earplug seat is provided with the second annular slot 7, so that the annular convex shoulder 4 on the earplug head is inserted in the second annular slot 7 more effectively, and efficiently prevents the earplug head from sliding down.

3. In the fitting between the earplug head and the earplug seat, components such as the earplug seat and the earplug head are visible, so a match of two colors of the earplug seat and the earplug head raises the visual profile of the earplug.

What is claimed is:

1. A stethoscope earplug seat, comprising:
a large tubular body having a first end and a second end opposite to each other, and defined by a first inner radius, a first outer radius and a first length; and
a small tubular body having a third end and a fourth end opposite to each other, and defined by a second inner radius, a second outer radius, and a second length,
wherein the large tubular body sheaths the small tubular body, and the first inner radius is equal to the second outer radius;
wherein the first length is smaller than the second length, the first end is located between the third end and the fourth end, and a second side surface of the second end is leveled with a fourth side surface of the fourth end;
wherein a first side surface and a first inner surface of the first end are concavely formed with a first annular slot, the first annular slot is defined by a third inner radius and a third outer radius, the third inner radius is equal to the first inner radius, and the third outer radius is smaller than the first outer radius; and
wherein a part of an outer surface of the small tubular body adjacent to the third end is concavely formed with a second annular slot, and the second annular slot has a fourth inner radius greater than the second inner radius and smaller than the second outer surface.

2. The stethoscope earplug seat according to claim 1, wherein an inner wall of the small tubular body is provided with a screw thread.

3. A fitted configuration, comprising:
an earplug head, comprising:
a spherical body defining a spherical space; and
a tubular body having a fifth end and a sixth end opposite to each other, and defined by a fifth inner radius and a fifth outer radius,
wherein the tubular body is integrally formed with the spherical body and connected with the spherical body through the fifth end, and an inner space defined by the tubular body is in communication with the spherical space defined by the spherical body;
wherein an inner surface portion of the fifth end is extended to form an annular convex shoulder, and the annular convex shoulder has an inner shoulder radius smaller than the fifth inner radius;
wherein a sixth side surface and a sixth outer surface of the sixth end are concavely formed with a third annular slot, the third annular slot has a sixth inner radius, the sixth inner radius is greater than the fifth inner radius and smaller than the fifth outer radius, such that a third protrusion is formed inside the third annular slot, and an inner radius of the third protrusion is equal to the fifth inner radius, and an outer radius of the third protrusion is equal to the sixth inner radius; and
an earplug seat, comprising:
a large tubular body having a first end and a second end opposite to each other, and defined by a first inner radius, a first outer radius and a first length; and
a small tubular body having a third end and a fourth end opposite to each other, and defined by a second inner radius, a second outer radius, and a second length,
wherein the large tubular body sheaths the small tubular body, and the first inner radius is equal to the second outside radius;
wherein the first length is smaller than the second length, the first end is located between the third end and the fourth end, and a second side surface of the second end is leveled with a fourth side surface of the fourth end;

wherein a first side surface and a first inner surface of the first end are concavely formed with a first annular slot, the first annular slot is defined by a third inner radius and a third outer radius, the third inner radius is equal to the first inner radius, and the third outer radius is smaller than the first outer radius, such that a first protrusion is formed surrounding the first annular slot, and an inner radius of the first protrusion is equal to the third outer radius, and an outer radius of the first protrusion is equal to the first outer radius;

wherein a part of an outer surface of the small tubular body adjacent to the third end is concavely formed with a second annular slot, and the second annular slot has a fourth inner radius greater than the second inner radius and smaller than the second outer surface; and wherein the third outer radius is substantially equal to the sixth inner radius, the fifth inner radius of the tubular body of the earplug head is slightly smaller than or equal to the second outer radius of the small tubular body, the fourth inner radius is substantially equal to the inner shoulder radius, such that when the earplug head is fitted into the earplug seat, a part of the small tubular body is inserted into the inner space of the tubular body, the first protrusion fits in the third annular slot, the third protrusion fits in the first annular slot, and the annular convex shoulder fits in the second annular slot.

4. The fitted configuration of claim 3, wherein a length of the third protrusion in a direction parallel to a longitudinal axis of the tubular body is equal to a length of the first annular slot in a direction parallel to a longitudinal axis of the large tubular body.

5. The fitted configuration of claim 3, wherein the first outer radius is substantially equal to the fifth outer radius.

* * * * *